United States Patent [19]

Chaffringeon et al.

[11] Patent Number: 5,919,232
[45] Date of Patent: Jul. 6, 1999

[54] PROSTHETIC FABRIC

[75] Inventors: Bernard Chaffringeon, Saint-Sulpice, Switzerland; Jean-Claude Sgro, Dijon, France

[73] Assignee: Cogent, Villefranche sur Saone, France

[21] Appl. No.: 08/737,628

[22] PCT Filed: May 23, 1995

[86] PCT No.: PCT/FR95/00675

§ 371 Date: Jun. 25, 1997

§ 102(e) Date: Jun. 25, 1997

[87] PCT Pub. No.: WO95/32687

PCT Pub. Date: Dec. 7, 1995

[30] Foreign Application Priority Data

May 27, 1994 [FR] France ................................. 94 06910
Oct. 19, 1994 [FR] France ................................. 94 12700

[51] Int. Cl.⁶ ....................................................... A61F 2/02
[52] U.S. Cl. ............................. 623/11; 600/37; 606/151; 606/153
[58] Field of Search ............................... 623/11; 600/37; 606/151, 153

[56] References Cited

U.S. PATENT DOCUMENTS 3,791,436  2/1974  Weckbrodt .
4,854,316  8/1989  Davis .
5,150,706  9/1992  Cox et al. .................................. 600/37
5,697,978  12/1997  Sgro ......................................... 606/151

FOREIGN PATENT DOCUMENTS

A 578 997    1/1994  European Pat. Off. .
A-2 200 379  8/1988  United Kingdom .
WO 92/06639  4/1992  WIPO .

OTHER PUBLICATIONS

A. Manuila et al., "Dictionaire Francais De Medecine et de Biologie" 1972, Masson et Cie, Paris, France, 4 pages.

*Primary Examiner*—Paul B. Prebilic
*Attorney, Agent, or Firm*—Oliff & Berridge, PLC

[57] ABSTRACT

A prosthetic fabric comprises a sheet textile structure capable of two different shapes, one being a flat, unfolded arrangement and the other being an ordered, gathered arrangement, and at least one continuous filiform element having two free gripping ends. The continuous filiform element is connected to the sheet structure by a plurality of catching points distributed over a surface of the sheet, along and on either side of a neutral axis that is parallel to one of the principal dimensions of the sheet. The structure of the fabric is such that pulling on the two gripping ends of the continuous filiform element generates the folded arrangement wherein the sheet is ordered transversely and on either side of the neutral axis and pulling on only one gripping end of the continuous filiform element extracts the continuous filiform element from the sheet.

16 Claims, 5 Drawing Sheets

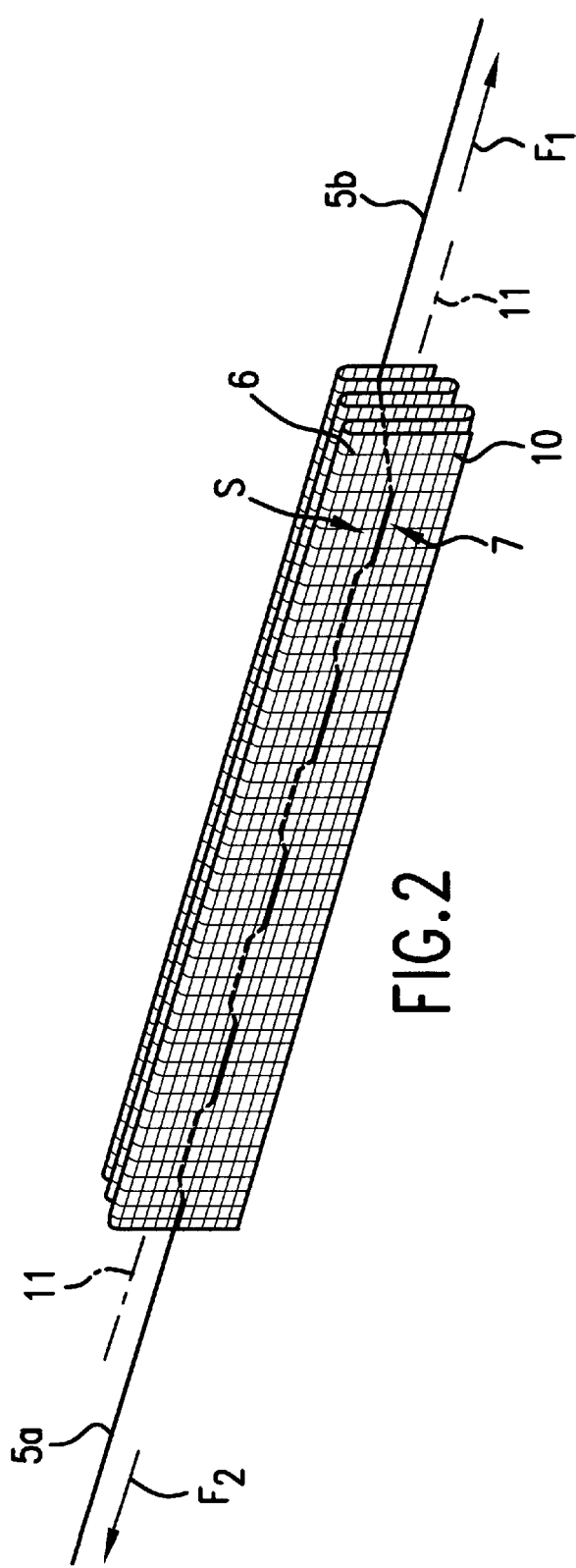
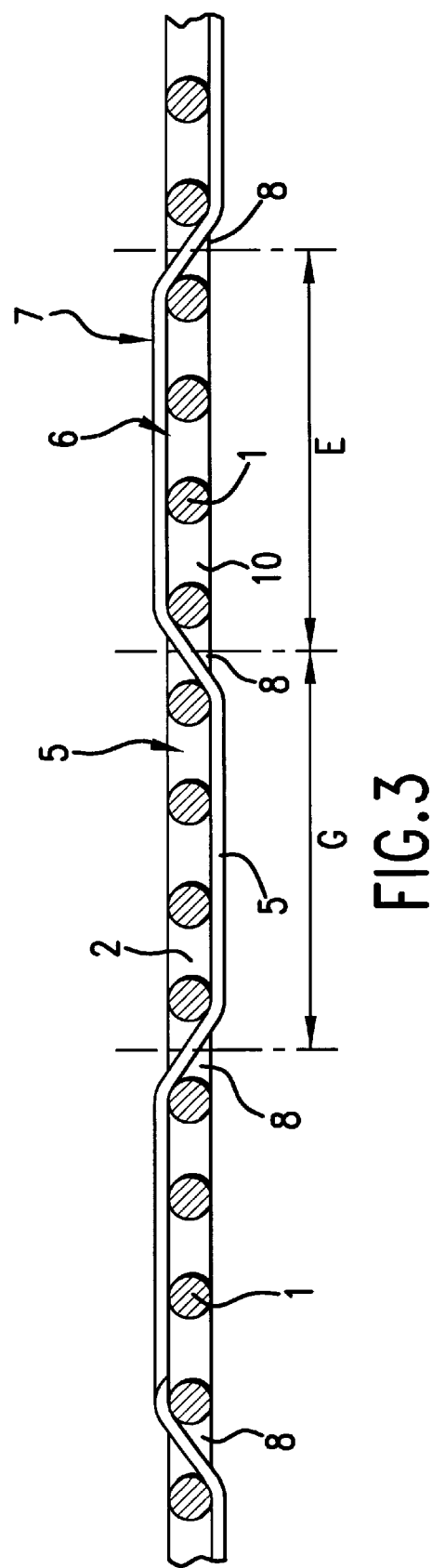

PROSTHETIC FABRIC

This application is a national stage application under 35 C.F.R. 371 of international application number PCT/FR95/00675 filed May 23, 1995.

The present invention relates to a prosthetic fabric, which can be used especially as an implantable parietal prosthesis in a human being, for example for a laparoscopic herniorrhaphy, via an extraperitoneal route.

In accordance with document WO-A-92 06639, a prosthetic fabric has been described which comprises:

a sheet with a textile structure, consisting of an interlacing or interweaving of wrap and weft threads, defining between them meshes which may possibly be blocked, the density of which is chosen in order to obtain an airy textile structure; the sheet, having a quadrangular general shape, is capable of adopting two different conformations, one being a compact conformation suitable for passing through a trocar, in which conformation the various parts of the sheet are gathered together into a form other than substantially plane, especially tubular, and the other being a deployed conformation, in which the same parts of the sheet open out substantially flat;

a continuous filiform element, joined onto the textile structure of the sheet while at the same time remaining free with respect to the latter, describing, when flat, a continuous line in the form of a loop, extending along the two dimensions of the sheet, being held on the latter in a plurality of catching points distributed along said continuous line.

The filiform element of WO-A-92 06639 constitutes in fact a reinforcement of the sheet, being at a same time rigid and flexible, although free with respect to the latter. This reinforcement makes it possible to direct the movements and orientation of the sheet, but not its change into the compact conformation (cf. FIG. 7), which requires an external action.

Moreover, the problem of the sheet as described in this document is that the folding is preformed irregularly, by the external action of withdrawing the loop through the insertion tubing. In this case, the loop takes the form of a drop or a tear, which means that the fabric is not folded in an ordered manner. This causes problems when it is freed in the extraperitoneal space, since it does not unfolding a uniform manner either, requiring additional positioning movement on the part of the surgeon, using the semi-rigid loop to direct the sheet to the correct place; this increases the risks of rupturing the peritoneum and of perforating the organs.

Other documents, especially document GB-A-2,200,379 and documents U.S. Pat. No. 3,791,436, in the field of domestic textiles, especially textiles for furnishing, describe various ways of folding fabrics to confer on them merely a particular decorative effect.

Those skilled in the art of prosthetic fabrics, and skilled in the surgical and medical art, would fail to identify and find in the field of ordinary textiles useful solutions in the field of surgical prostheses.

The object of the present invention is to improve a prosthetic fabric as described in document WO-A-92 06639, and more particularly to make it easier to change in an ordered manner from the deployed conformation to the compact conformation of the sheet with a textile structure.

In accordance with the present invention, the catching points holding the filiform element onto the sheet are distributed over the surface of the latter, along and on either side of a neutral axis, parallel to one of the principal dimensions of said sheet, so that any pulling of said filiform element via a free gripping end, with said element sliding with respect to the conformationally free sheet, generates positively an ordered folded arrangement of said sheet, in its compact conformation, transversely and on either side of said neutral axis.

In fact, one of the advantages of the prosthetic fabric according to the present invention is that it allows order gathering of the sheet which, in its compact conformation, is subsequently inserted easily into a trocar or inserting tube. Furthermore, the specific folded arrangements of the sheet make it easier to position it, for example in the extraperitoneal space, since the surgeon has only to withdraw the gathering thread and the sheet deploys in a regular manner at the correct place, without requiring particular intervention by the surgeon. This is because the filiform element is neither braked nor blocked when extracting it from the sheet in its compact conformation, but lets itself be easily withdrawn without puckering or blocking.

A prosthetic fabric according to the present invention therefore incorporates a positive means for changing from the depolyed conformation to the compact conformation, while maintaining, moreover, the other properties or functions of said prosthetic fabric.

The present invention will not be described with reference to the appended drawing, in which:

FIG. 2 represents a perspective view of the prosthetic fabric shown in FIG. 1, in its compact conformation;

FIG. 3 represents a sectional view, on a large scale, on the line III—III in FIG. 1, of the prosthetic fabric in its conformation shown in FIG. 1;

Figure 1:
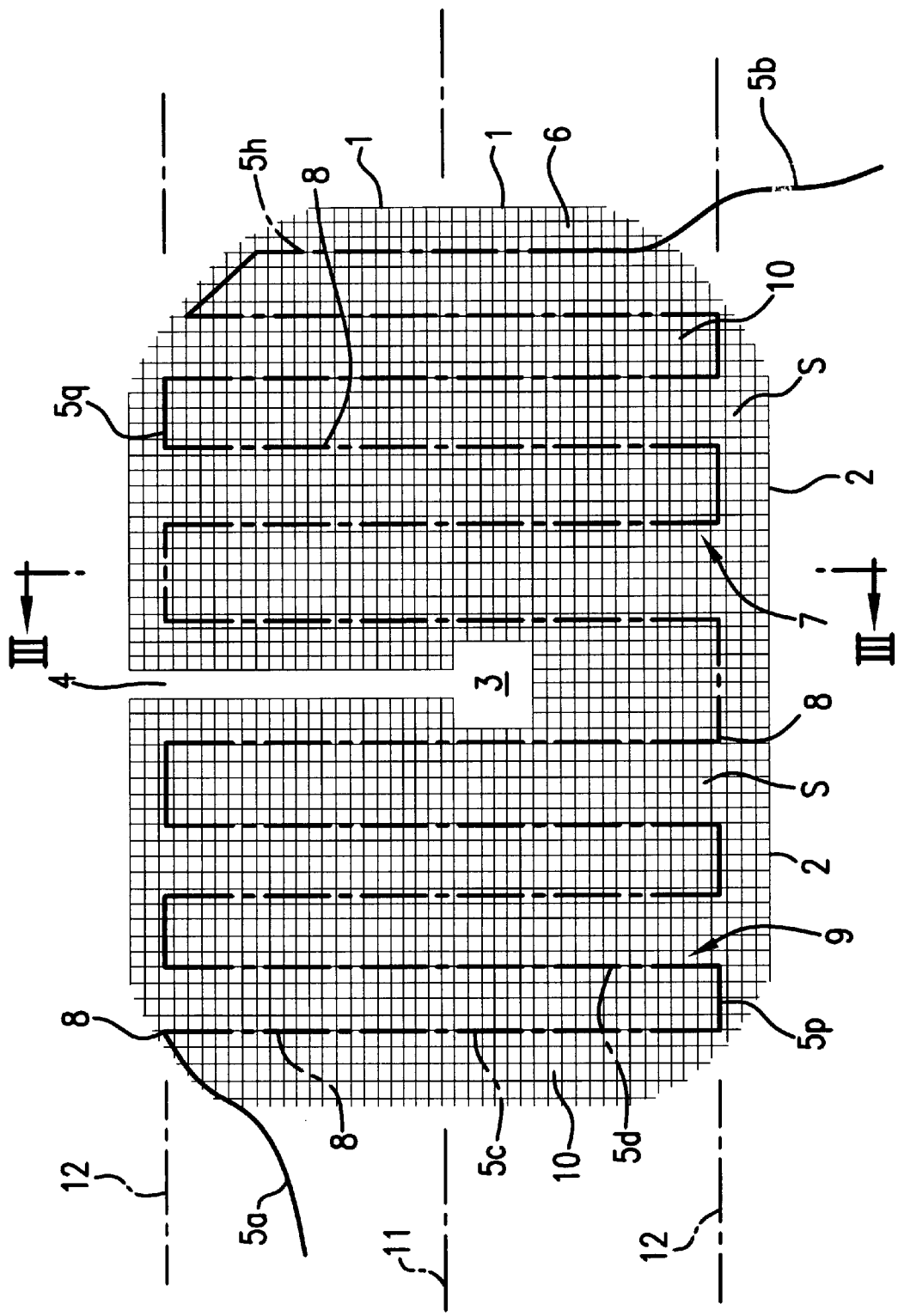
FIG. 1 represents a flat view, in the deployed conformation, of a prosthetic fabric in accordance with the invention.

In accordance with FIGS. 1 to 3, a prosthetic fabric according to the invention comprises:

a sheet 6 with a textile structure S, consisting of a fabric, and consequently an interlacing of warp threads 1 and of weft threads 2, producing between them meshes 10; the sheet 6 has a quadrangular and more particularly rectangular general shape; and, as shown in FIGS. 1 and 2, it is capable of adopting two different conformations, one being a compact conformation (cf. FIG. 2) in which various longitudinal parts or portions of the sheet are gathered together and folded into a form other than substantially plane, for example an elongate parallepipedal shape, and the other being a deployed conformation (cf. FIG. 1), in which the same longitudinal parts of the sheet open out substantially flat;

at least one continuous filiform element 5 for bringing together, in the compact conformation, the various longitudinal parts of the sheet, comprising two free ends 5a and 5b, respectively at the two longitudinal ends of the sheet, forming one and the same thread with the free gripping ends 5a and 5b, which is, as described hereinbelow, joined onto the textile structure S of the sheet, while at the same time remaining free to slide with respect to the latter.

When the sheet 6 is used for a laparascopic herniorrhaphy it has, in its central part, an opening 3 connected to a longitudinal edge by a transverse slit 4. The density of the textile structure S is chosen so as to obtain an airy structure, through the meshes of which the previously described filiform element 5 can pass freely, successively above and below the sheet 6. The warp threads 1 and the weft threads 2 are biocompatible and may have a certain degree of elasticity giving the sheet 6 a memory of the shape in the deployed conformation. In some cases, the threads 1 and 2 may be chosen from an absorbable material, it being understood that the airy structure of the sheet allows colonization and fixation by cells in vivo. By way of example, the threads 1 and 2 may be made of polyester and are coated with collagen or with any other substance having a trophic effect with respect to cells.

The filiform element 5, separate from the warp threads 1 and the weft threads 2, describes, when flat, a continuous line alternating, pseudo-sinusoidally, along the length and the width of the sheet, occupying virtually the entire surface of the latter. The filiform element 5 is held on the textile structure S in a plurality of catching points 8, each corresponding to the filiform element passing through a mesh, toward the top or the bottom of the structure S, and these catching points 8 are distributed uniformly along the pseudo-sinusoidal continuous line 9. As shown in FIG. 3, the catching points 8 are uniformly spaced apart along the width of the sheet 6, by equal intervals E and G, this modality being of a secondary nature.

In accordance with the invention, and as may be more clearly seen by comparing FIGS. 1 and 2, the sheet 6 has a neutral axis 11 on the textile structure 6, parallel to the length of the latter, and passing substantially through the middle of the said sheet. The catching points 8 defined above are distributed, as described hereinbelow, over the surface of the sheet 6 and with respect to the neutral axis 11 so that pulling, along the direction of the arrows F1 and F2 in FIG. 2, on the two gripping ends 5a and 5b respectively, preferentially generates a translationally ordered folded arrangement of the sheet 6, transversely with respect to the neutral axis 11 and on either side of the latter.

The neutral axis 11 lies parallel to the warp threads 1 which are themselves arranged along the length of the sheet 6, in such a way that threads 1 can act as folding initiators. The neutral axis 11 could lie parallel to the waft threads 2, these lying along the width of the sheet 6.

As shown in FIG. 1, the catching points 8 of the filiform element 5 are distributed on either side of the neutral axis 11, and along the latter. More precisely, the catching points 8 define, in pairs, transverse sections 5c, 5d, 5e, 5n, arranged perpendicular to the neutral axis 11 and distributed along the latter; these transverse segments are continuously joined at their ends, on the one hand, to the two gripping ends 5a and 5b with regard to the first segment 5c and last segment 5n respectively and, on the other hand, to each other, alternately, by longitudinal segments 5p and 5q parallel to the neutral axis. Given the above arrangement, the catching points 8 define two lines of connection 12 with the textile structure S of the sheet 6, these lines being parallel to and on either side of the neutral axis 11; these lines of connection 12 are substantially equidistant from the neutral axis 11. The transverse segments 5c to 5n may or may not be equal, and the same applies to the longitudinal segments 5p and 5q.

Figure 4:
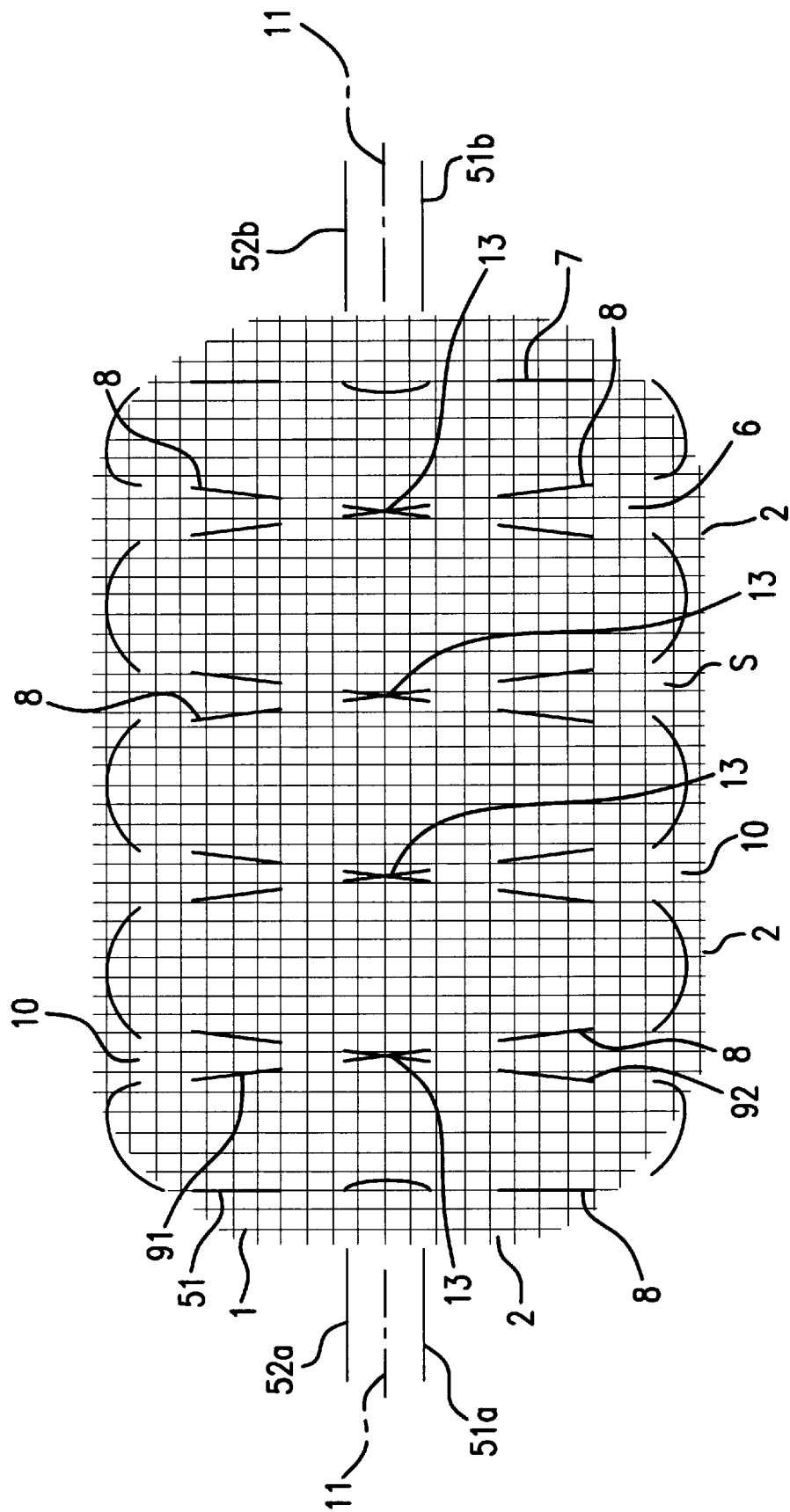
FIG. 4 represents, in its deployed conformation, a prosthetic fabric in accordance with another embodiment of the present invention.

The filiform element 5 and the sheet 6 are arranged freely with respect to each other in order to allow extraction of the filiform element in the compact conformation of the sheet shown in FIG. 2, for example by pulling on the end 5b in the direction of the arrow F1. The embodiment in FIGS. 4 to 6 differs from that shown in FIGS 1 to 3 only by the following characteristics:

filiform means 7, for bringing together the sheet into the compact conformation, comprise two opposed filiform elements 51 and 52, each describing, when flat, approximately a sinusoid or a zigzag, on either side of the neutral axis of the textile structure S, the two sinusoids or zigzags, in phase opposition as it were, crossing each other in a plurality of points 13 which lie on the neutral axis 11;

each filiform element 51 or 52 has its own gripping ends, namely 51a and 51b, or 52a and 52b, which may possibly be linked to each other in order to distribute the pulling force;

the two opposed filiform elements 51 and 52 form a geometrical figure which is symmetrical with respect to the neutral axis.

Figure 5:
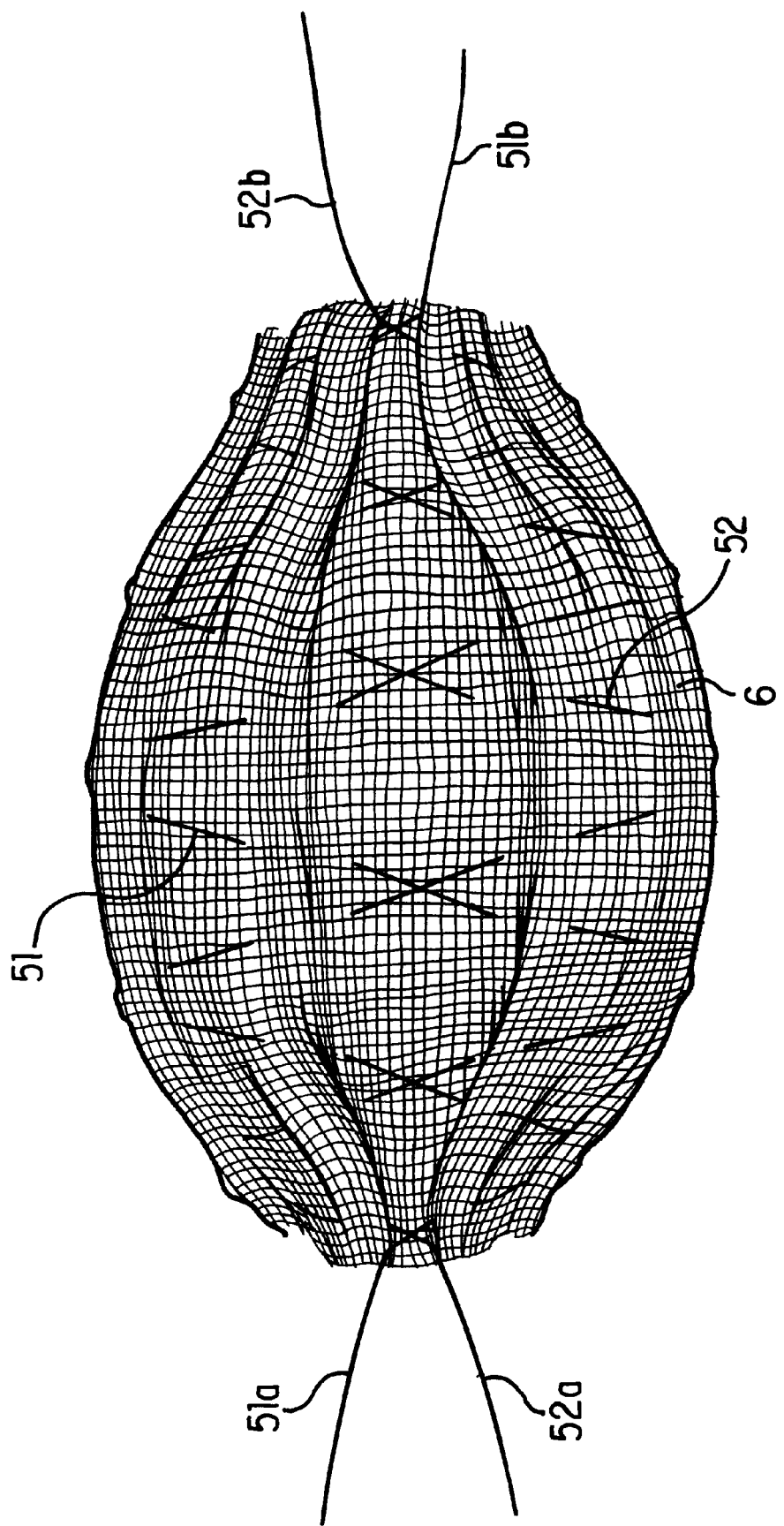
FIG. 5 represents, front on, a prosthetic fabric of FIG. 4 in a conformation intermediate between the flat deployed conformation in FIG. 4 and the compact conformation in FIG. 6.
Figure 6:
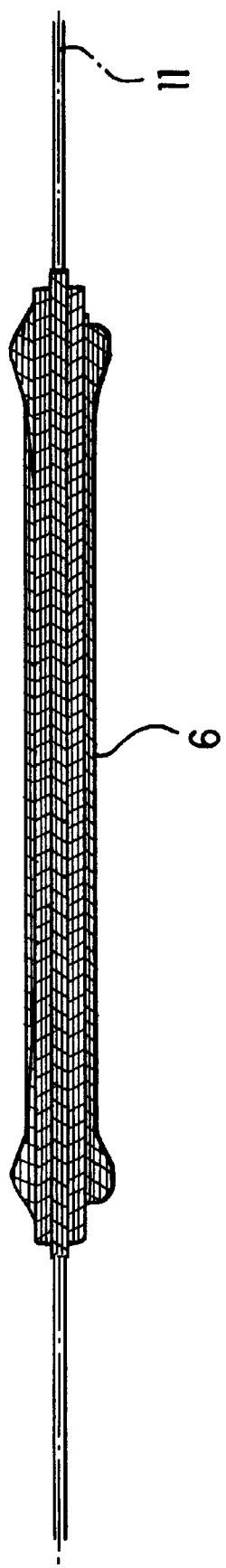
FIG. 6 represents the prosthetic fabric of FIG. 4 in its compact conformation.

By pulling on the ends 52a and 51a, in opposition to the pulling force exerted at the same time on the ends 52b and 51b, the prosthetic fabric firstly adopts a conformation as shown in FIG. 5, and then the fully compact conformation shown in FIG. 6, which is compatible with passing through a trocar for example. Then, by extracting the filiform elements 51 and 52, after passing through the trocar, the fabric may once again be deployed, for example in the peritoneal cavity.

In another application example, the sheet in its compact conformation may also be first of all inserted into a tubular guide, which is itself subsequently inserted into a trocar so as to make it easier to position the sheet.

Finally, it will be noted that the prosthetic fabric as described above can be used in other surgical interventions, for example in gynecology, and using the same folding principle, with however the modification that the fabric is firstly attached to the edges of a muscle tear, such as in the uterine wall, in its already-deployed conformation, and that subsequently the ends of the filiform element are pulled so as to gather the sheet and thus bring the edges of said muscle tear together. In this case, the threads of the filiform element, which may be biocompatible or absorbable, are not cut but remain inside the body.

We claim:

1. A prosthetic fabric comprising a sheet with a biocompatible, implantable textile structure conformable from a flat arrangement to a folded arrangement having a memory of the flat arrangement, and at least a continuous filiform element joined onto the textile structure of the sheet while also remaining free to slide with respect to the sheet, the continuous filiform element having first and second free gripping ends, wherein the continuous filiform element defines in the flat arrangement of the sheet a continuous line along at least on dimension of said sheet, wherein the continuous filiform element in joined onto the sheet with a plurality of catching points distributed along said continuous line, wherein the catching points are distributed over a surface of the sheet, along and on each side of a neutral axis, parallel to one of the principal dimensions of said sheet, wherein pulling on the two gripping ends of the continuous filiform element generates the folded arrangement of the sheet, ordered transversely and on each side of said neutral axis, and wherein pulling one gripping end of the continuous filiform element in either the flat arrangement or the folded arrangement of the sheet allows extraction of the continuous filiform element.

2. The fabric as claimed in claim 1, in which the textile structure of the sheet consists of an interlacing of warp threads and of weft threads that forms meshes, wherein the neutral axis lies parallel to the warp threads or to the weft threads.

3. The fabric as claimed in claim 2, wherein the neutral axis passes substantially through the middle of the sheet.

4. The fabric as claimed in claim 3, wherein the catching points define, in pairs, transverse segments arranged perpendicular to the neutral axis and distributed along the neutral axis, wherein a first transverse segment is joined at an end thereof to the first gripping end, a last transverse segment is joined at an end thereof with the second gripping end, and remaining transverse segments are joined at ends thereof to each other alternately by longitudinal segments parallel to the neutral axis.

5. The fabric as claimed in claim 4, wherein the catching points define two lines of connection with the textile structure of the sheet, these lines being parallel to and on each side of the neutral axis.

6. The fabric as claimed in claim 5, wherein the lines of connection are substantially equidistant from the neutral axis.

7. The fabric as claimed in claim 4, wherein the transverse segments are equal in length.

8. The fabric as claimed in claim 4, wherein the longitudinal segments are equal in length.

9. The fabric as claimed in claim 1, wherein two opposed filiform elements each describe, when flat, approximately a sinusoid or a zigzag, on either side of the neutral axis, the two sinusoids or zigzags crossing each other in a plurality of points lying on the neutral axis.

10. The fabric as claimed in claim 9, wherein the two opposed filiform elements form a geometrical figure which is symmetrical with respect to the neutral axis.

11. The fabric as claimed in claim 9, wherein each opposed filiform element is connected at both ends to two free gripping ends, respectively.

12. The fabric as claimed in claim 1, wherein the filiform element and the sheet are designed to allow extraction of the filiform element, in the folded arrangement of the sheet.

13. The fabric as claimed in claim 4, wherein the transverse segments have different lengths.

14. The fabric as claimed in claim 4, wherein the longitudinal segments have different lengths.

15. The fabric as claimed in claim 1, wherein the fabric has a size capable of passing through a trocar and of being deployed in a peritoneal cavity.

16. The fabric as claimed in claim 1, wherein the two gripping ends of the continuous filiform element are located at opposite ends of the fabric.

* * * * *